United States Patent [19]

Krzeminski

[11] 4,121,572

[45] Oct. 24, 1978

[54] UTERINE SOUND

[75] Inventor: Melvin L. Krzeminski, Palatine, Ill.

[73] Assignee: G.D. Searle & Co., Chicago, Ill.

[21] Appl. No.: 766,316

[22] Filed: Feb. 7, 1977

[51] Int. Cl.² ............................................. A61B 5/10
[52] U.S. Cl. ................................... 128/2 S; 33/169 B
[58] Field of Search .................... 128/2 S, 2 R, 361; 33/174 D, 169 B

[56] References Cited

U.S. PATENT DOCUMENTS

| | | | |
|---|---|---|---|
| 1,856,295 | 5/1932 | Sovatkin | 128/361 |
| 2,241,451 | 5/1941 | Fist | 128/25 X |
| 3,297,030 | 1/1967 | Czorny et al. | 128/214.4 |
| 3,559,643 | 2/1971 | Pannier, Jr. | 128/214.4 |
| 3,706,307 | 12/1972 | Hasson | 128/2 S |
| 4,016,867 | 4/1977 | King et al. | 128/2 S |

Primary Examiner—Kyle L. Howell
Attorney, Agent, or Firm—John A. Dhuey

[57] ABSTRACT

A uterine sound is described having a probe with measuring indicia inscribed thereon and a horseshoe-shaped body slidable along said probe and cooperative therewith for measurement of uterine position and dimension. A raised rib is located along a substantial length of the probe to normally retain the horseshoe-shaped body in parallel alignment with the longitudinal axis of the probe. When the body is displaced from parallel alignment with the probe, the rib interacts with the body to fix the body relative to the probe, and permit withdrawal of the probe and body as a unit. An internal stop mechanism is employed to prevent excessive movement of the body relative to the probe.

7 Claims, 5 Drawing Figures

UTERINE SOUND

The present invention is concerned generally with gynecological instruments. In particular, it is concerned with improvements in those instruments adapted for dimensional and positional measurement of the uterine cavity.

Prior art instruments have consisted of a probe which is slidable within a tubular body, the probe having measuring indicia along its length. In use, the conventional probe is inserted into the uterus until its distal end reaches the uterine fundus. Then the tubular body is moved upwardly until it contacts the cervical os. Measuring indicia are so arranged on the probe that one must determine the dimensional reading from the location of the bottom of the tubular body on the probe while the device is in the uterus. In many situations, the indicia on the probe become positioned such that they are difficult to read when the probe is located in the cervical canal. Consequently, it is desirable to have some means of locking the body to the probe so that both can be removed as a unit without changing their relative positions. After removal an accurate reading can be made from the exposed indicia adjacent the end of the tubular body.

The present invention is directed to such an improved uterine sound having a simple and economical locking means. Furthermore, an internal stop means is provided to prevent excessive movement of the body on the probe. Provision for the stop means internally provides for ease in assembly of the probe and body and minimizes the number of external protuberances on the sound.

The invention will be described with reference to the following drawings in which.

Figure 1:
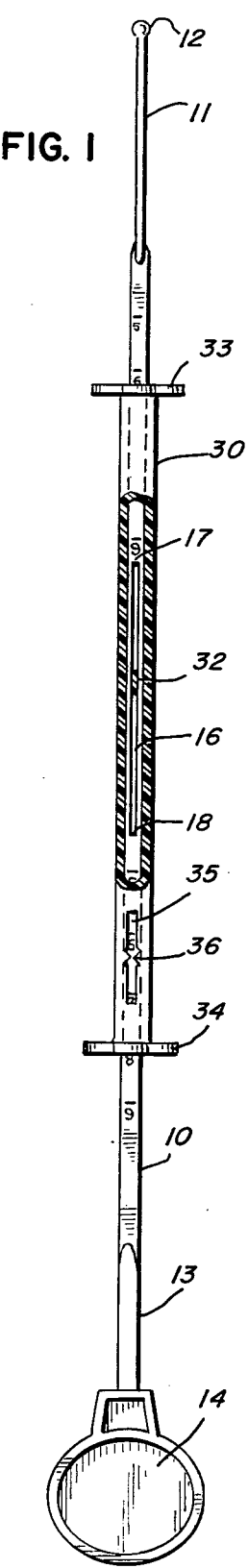
FIG. 1 is a plan view of the device partially cut away to illustrate the inner stop means on the device.

With reference to those drawings, the instrument of this invention comprises a probe 10 and a body 30. Probe 10 is an elongated shaft having a distal end 11, which is generally rounded, preferably terminating in spherically-shaped nub 12, and a proximal end 13, which terminates in a finger-grip 14. Body 30 is generally horseshoe-shaped having inwardly curved sides 31. Sides 31 are adapted to encompass ribs 15 on probe 10. Ribs 15 extend substantially the length of probe 10 and are positioned at opposite sides thereof. Projection 32 on body 30 extends inwardly of body 30 and is adapted to slidably move within channel 16 in probe 10. Channel 16 extends only an intermediate distance along probe 10 and terminates at ends 17 and 18, which provide a stopping means in conjunction with projection 32 to prevent body 30 from being pushed upwardly in an excessive manner and from sliding too far down along probe 10.

In a most preferred embodiment, the stopping means limits relative movement of the body on the probe between almost five to nine centimeters to accommodate the typically sized uterus.

In a preferred embodiment, boby 30 has flanges 33 and 34 at its distal and proximal ends, respectively, and a viewing aperture or window 35 having a pointer 36 associated therewith. The viewing window, pointer and indicia are positioned so that the indicia present opposite the pointer represents the distance from the distal end of probe 10 to the distal end of body 30. Furthermore, the viewing window generally is made large so that several indicia can be seen to facilitate reading when the pointer is between the numbers on the probe.

In an especially preferred embodiment, flange 33 is annular and is adapted to encompass probe 10 when body 30 is placed thereon while permitting body 30 to slide upon probe 10.

Figure 2:
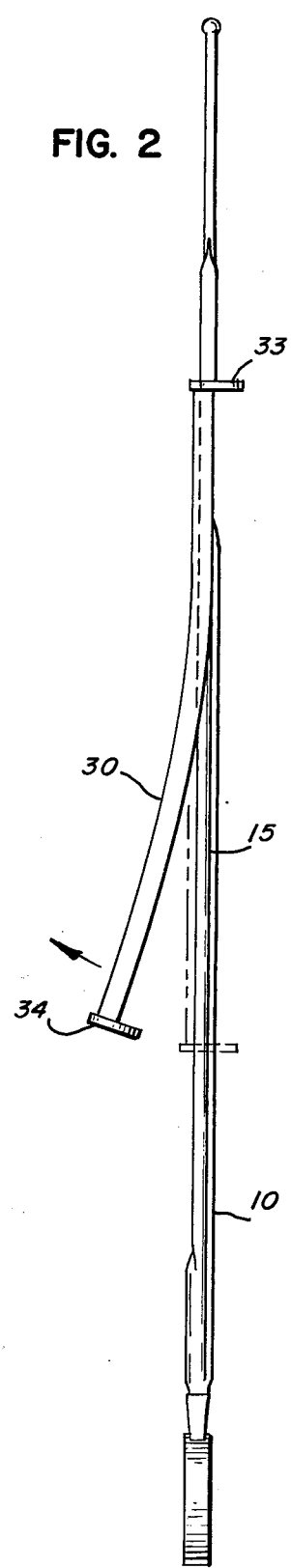
FIG. 2 is a side view of the device illustrating the relative position of the probe and body in the lock position.
Figure 3:
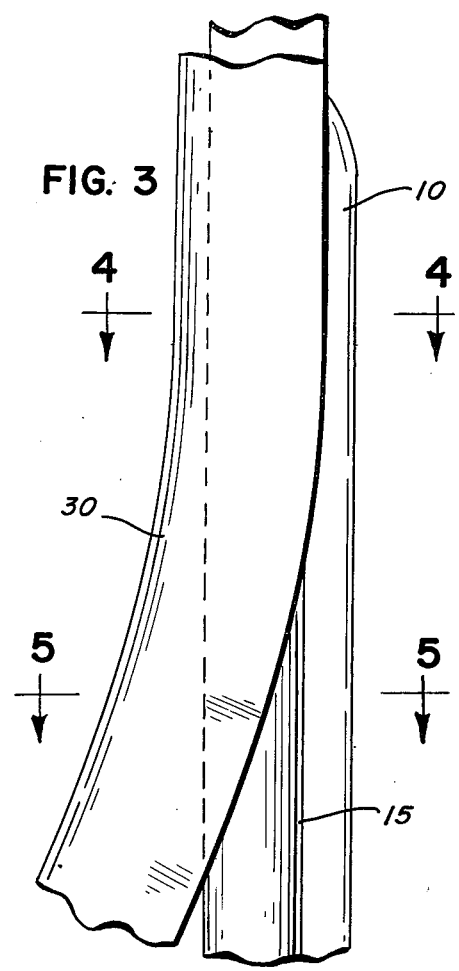
FIG. 3 is an enlarged view of the device in the area at which the probe and body lock.
Figure 4:
FIG. 4 is a sectional view along line 4—4 illustrating the unlocked positions of the probe and body.
Figure 5:
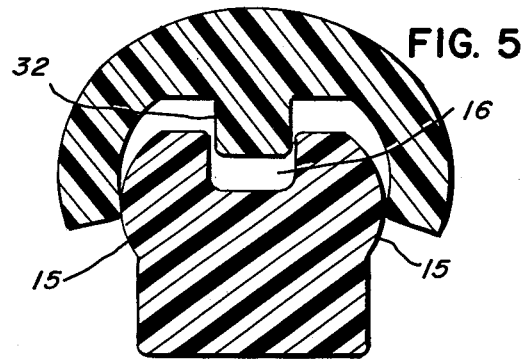
FIG. 5 is a sectional view along line 5—5 illustrating the locked positions of the probe and body.

FIGS. 2-5 illustrate the device in its two operative modes. In the first mode, body 30 is positioned in probe 10 such that their longitudinal axes are parallel to each other. In the second mode, the proximal end of body 30 is displaced from probe 10 such that sides 31 of body 30 impinge upon ribs 15 of probe 10, as shown most clearly in FIGS. 2 and 5. Sides 31 are sufficiently resilient to bend outwardly when body 30 is moved to its displaced position. The inwardly directed forces created by sides 31 acting upon ribs 15 are sufficient to keep body 30 and probe 10 in fixed relative axial positions when the instrument is removed from the cervical canal.

In its normal, first position, body 30 is slidably movable upon probe 10 along the distance proscribed by stops 17 and 18. Projection 32 not only interacts with stops 17 and 18 in channel 16, but it also orients body 30 on probe 10 so that the indicia scribed on probe 10 can be observed through viewing window 35.

The present device is conveniently manufactured from moldable plastic materials such as polypropylene and the like. The device is molded in two parts and assembled by forcing body 30 over probe 10 such that sides 31 encompass ribs 15. The natural resiliency of sides 31 permit such a snap-fit arrangement. The uterine sound then is packaged in a conventional manner and sterilized so that it is ready for use.

What is claimed is:

1. A uterine sound comprising:

an elongated probe having a distal end and a proximal end, measuring indicia scribed thereon between said distal and proximal ends and an integral, raised first rib extending substantially the length thereof; and an elongated body having a distal end and a proximal end mounted on said probe, said body being of horsehoe-shaped cross-section and having inwardly curved sides, at least one of said sides encompassing said first rib and cooperating therewith to retain said body on said probe at a first position whereat said body is parallel to the longitudinal axis of said probe and is slidably moveable along said probe, and said cooperating side being adapted to engage said first rib and cooperate therewith to hold said body on said probe at a second position whereat the proximal end of said body is displaced from said probe and said body is restrained from slidably moving along said probe.

2. A uterine sound as in claim 1 further comprising a second integral, raised rib on said probe extending substantially the length thereof, each side of said body encompassing one of said ribs and cooperating therewith to retain said body on said probe at said first position and each of said sides being adapted to engage one of said ribs and cooperate therewith to hold said body on said probe at said second position.

3. A uterine sound as in claim 2 wherein said first and second ribs are located on opposite sides of said probe and further comprising an inwardly extending projection on the inner surface of said body and an opposed channel on said probe, said projection and said channel being adapted to cooperatively engage and permit said projection to slide axially in said channel.

4. A uterine sound as in claim 3 further comprising a viewing aperture in said body and a pointer associated therewith, said indicia indicating the distance from the distal end of said probe to the distal end of said body.

5. A uterine sound as in claim 4 wherein said viewing aperture simultaneously exposes at least two indicia within the aperture.

6. A uterine sound as in claim 1 further comprising stop means on said sound comprising an inwardly extending projection on the inner surface of said body and an opposed channel on said probe, said projection and said channel being adapted to cooperatively engage and permit said projection to slide axially in said channel.

7. A uterine sound as in claim 6 wherein said projection and channel are rectangular in cross-section.

* * * * *